(12) United States Patent
Ahmed et al.

(10) Patent No.: US 8,734,426 B2
(45) Date of Patent: May 27, 2014

(54) LOCKING ASSEMBLY FOR A DRAINAGE CATHETER

(75) Inventors: Mahfuza Ahmed, Bloomington, IN (US); Tyler J. Bunch, Bloomington, IN (US); Charles W. Agnew, West Lafayette, IN (US); Kate Duncan, Mooresville, IN (US); James B. Hunt, Bloomington, IN (US); Bonita L. Nickless, Spencer, IN (US); Nancy L. Hutchinson, Spencer, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 446 days.

(21) Appl. No.: 12/905,254

(22) Filed: Oct. 15, 2010

(65) Prior Publication Data

US 2011/0098682 A1    Apr. 28, 2011

Related U.S. Application Data

(60) Provisional application No. 61/254,012, filed on Oct. 22, 2009.

(51) Int. Cl.
*A61M 27/00* (2006.01)

(52) U.S. Cl.
USPC .......................................................... 604/544

(58) Field of Classification Search
USPC .............. 604/541–544, 528, 95.04; 600/585, 600/146, 149; 623/1.11; 606/108, 272
See application file for complete search history.

(56) References Cited

U.S. PATENT DOCUMENTS

| 4,643,720 | A | 2/1987 | Lanciano |
| 5,399,165 | A | 3/1995 | Paul, Jr. |
| 5,489,269 | A | 2/1996 | Aldrich et al. |
| 5,637,102 | A | 6/1997 | Tolkoff et al. |
| 5,989,241 | A | 11/1999 | Plishka et al. |
| 6,159,177 | A | 12/2000 | Amos, Jr. et al. |
| 6,299,598 | B1 | 10/2001 | Bander |

(Continued)

FOREIGN PATENT DOCUMENTS

| EP | 0343910 | 6/1993 |
| WO | WO92/07215 | 4/1992 |
| WO | WO2011/066113 | 6/2011 |

OTHER PUBLICATIONS

International Search Report, issued in PCT/US2010/056437, dated Jun. 3, 2011.

(Continued)

*Primary Examiner* — Tan-Uyen T. Ho
*Assistant Examiner* — Mark Wardas
(74) *Attorney, Agent, or Firm* — Brinks Gilson & Lione

(57) ABSTRACT

A drainage catheter includes an elongated tubular member, a locking assembly engaged with a proximal end of the tubular member, and a tension member for drawing a distal end of the tubular member into a desired configuration. The locking assembly includes a connector, a locking arm, and a locking mechanism. The connector has an exterior surface profile that corresponds with an interior surface profile of the locking arm. The locking arm is pivotably attached to the connector to enable pivoting movement of the locking arm between an unlocked position and a locked position whereby the tension member is secured between the locking arm and the connector when the arm is in the locked position. The locking assembly may alternatively comprise a connector and a sliding sleeve or a connector having a clamping element disposed therein.

11 Claims, 6 Drawing Sheets

(56) References Cited

U.S. PATENT DOCUMENTS

| | | |
|---|---|---|
| 6,454,740 B1 | 9/2002 | Mody |
| 6,508,789 B1 | 1/2003 | Sinnott et al. |
| 6,666,853 B2 | 12/2003 | Chu et al. |
| 6,699,233 B2 | 3/2004 | Slanda et al. |
| 7,087,038 B2 | 8/2006 | Lee |
| 7,217,256 B2 * | 5/2007 | Di Palma ............... 604/104 |
| 8,137,323 B2 * | 3/2012 | Rosenberg et al. ........... 604/174 |
| 2001/0049490 A1 | 12/2001 | Slanda et al. |
| 2002/0091303 A1 | 7/2002 | Ootawara et al. |
| 2004/0039339 A1 | 2/2004 | Magnusson |
| 2005/0107739 A1 | 5/2005 | Palma |
| 2006/0142695 A1 | 6/2006 | Knudson |
| 2006/0212023 A1 | 9/2006 | Cross |
| 2006/0217667 A1 | 9/2006 | Accisano, III et al. |
| 2007/0032779 A1 | 2/2007 | Accisano, III et al. |
| 2007/0049907 A1 * | 3/2007 | Fischer et al. .............. 604/544 |
| 2007/0078385 A1 | 4/2007 | Accisano, III et al. |
| 2007/0083189 A1 * | 4/2007 | Lampropoulos et al. ...... 604/541 |
| 2007/0118206 A1 * | 5/2007 | Colgan et al. .............. 623/1.11 |
| 2007/0203474 A1 | 8/2007 | Ryan |
| 2008/0125756 A1 | 5/2008 | Dicarlo et al. |
| 2008/0200839 A1 | 8/2008 | Bunch et al. |
| 2008/0242932 A1 | 10/2008 | Carter |
| 2008/0312599 A1 | 12/2008 | Rosenberg |
| 2009/0171295 A1 | 7/2009 | Porter et al. |

OTHER PUBLICATIONS

International Search Report, issued in PCT/US2010/052797, dated Dec. 8, 2010.

* cited by examiner

LOCKING ASSEMBLY FOR A DRAINAGE CATHETER

RELATED APPLICATIONS

This application claims the benefit of U.S. Provisional Application No. 61/254,012, filed Oct. 22, 2009, the entire content of which is hereby incorporated by reference herein.

TECHNICAL FIELD

This invention relates to drainage catheters and particularly to a locking mechanism for a drainage catheter for drawing and maintaining the distal end of the catheter into a desired configuration.

BACKGROUND

Suprapubic catheterization of the bladder is used to drain the bladder after surgery or when the genitourinary system is plugged by an obstruction. Other percutaneously inserted catheters are also used to drain the kidney or biliary system as well as to drain abscesses, other sites of fluid collection, and other viscera. Still other percutaneously inserted catheters are gastrostomy feeding tubes.

These catheters are typically introduced into the patient by means of a large hypodermic needle or trocar, which pierces the abdominal wall. A wire guide is inserted through the needle and then the needle is removed. The catheter tube with a stiffening cannula positioned therein is then passed over the wire guide into the cavity. The cannula and wire guide are withdrawn, leaving the catheter in the desired cavity. In addition, a dilator and an access sheath may be used alone or in combination with one another over the wire guide to increase the size of the puncture site before passing the catheter tube over the wire guide. With respect to the bladder, the advantage of this technique is that irrigation and infection of the urinary tract is minimized. However, one problem with these catheters is that the catheter can be easily pulled out by movement of the body or by the emptying of, for example, the bladder. Another problem is that side ports at the distal end of the catheter may be inadvertently drawn into the abdominal cavity, creating the potential for severe infections.

Various catheters have been developed with so-called pigtail loops at their distal ends for ensuring drainage of the cavity and preventing accidental removal therefrom. The pigtail loop is tightened by pulling on the proximal end of a flexible tension member, which extends through the catheter. The proximal end of this tension member is held in place by any one of a number of retention means. One known locking drainage catheter includes a lockable connector positioned about the proximal end of the catheter. The catheter also includes a flexible tension member that extends through the lockable connector for drawing the distal end of the catheter into a loop. The lockable connector includes a resilient material sleeve with a sleeve passage extending longitudinally therethrough for positioning the tension member therein. The sleeve is positioned in a passage of the connector adjacent a channel, wherein a pivotably attached lever is positioned. When the lever is pivoted toward the connector into a fixed position, a cam surface of the lever compresses the sleeve and locks thereabout to maintain the loop formed in the distal member end. Although the locking drainage catheter is well-suited for its intended purpose, the lockable connector portion of the catheter is somewhat bulky, which may make the device somewhat uncomfortable for a patient and which prevents the device from being used with relatively smaller sized access sheaths (e.g., a 30 Fr access sheath) unless the access sheath is altered or modified. It is desirable to provide a locking mechanism for use with a catheter, such as a drainage catheter, that overcomes the disadvantages present with available catheters and locking mechanisms.

SUMMARY OF THE INVENTION

In a first aspect, a locking assembly for use with a tension member in a drainage catheter includes a connector, a locking arm, and a locking mechanism. The connector is disposed at a proximal end of the catheter and has an exterior surface profile and a passageway extending longitudinally therethrough. The locking arm has an interior surface profile that corresponds with the exterior surface profile of the connector and is pivotably attached to the connector to enable pivoting movement of the locking arm about an axis of rotation, to and between an unlocked position and a locked position whereby when the locking arm is in the locked position, the tension member is secured between the interior surface of the locking arm and the exterior surface of the connector. The locking mechanism prevents the locking arm from inadvertently disengaging from the locked position.

In a feature of the first aspect, the exterior surface profile of the connector is cylindrical and the interior surface profile of the locking arm is curved to correspond with the cylindrical exterior surface profile of the connector. In another feature of the first aspect, the locking assembly is dimensioned to fit within a 30 Fr access sheath. In an additional feature, the connector includes an aperture through which a proximal portion of the tension member may pass. In a further feature, the locking arm may include a sealing element disposed on the interior surface thereof, wherein the sealing element prevents fluid contents of the catheter from inadvertently exiting the aperture when the locking arm is in the locked position. In other features, the locking arm may be attached to the connector with a pivot pin or with a living hinge, the locking mechanism may include an interference fit between the connector and the locking arm, and the locking mechanism may include a ridge and slot assembly.

In a second aspect of the invention, a drainage catheter includes an elongated tubular member and a locking assembly. The tubular member has a distal end for insertion into a patient, a proximal end, and a passageway extending longitudinally therethrough. The distal end is formed to be positioned into a desired configuration. The locking assembly is engaged with the proximal end of the tubular member and includes a connector, a locking arm, and a locking mechanism. The connector has an exterior surface profile and a passageway extending longitudinally therethrough. The locking arm has an interior surface profile that corresponds with the exterior surface profile of the connector and is pivotably attached to the connector to enable pivoting movement of the locking arm about an axis of rotation, to and between an unlocked position and a locked position whereby when the locking arm is in the locked position, a tension member is secured between the interior surface of the locking arm and the exterior surface of the connector. The locking mechanism prevents the locking arm from inadvertently disengaging from the locked position.

In a third aspect of the invention, a locking assembly for use with a tension member in a drainage catheter includes a tapered connector, a tapered locking sleeve, and a locking mechanism. The tapered connector has an exterior surface and a passageway extending longitudinally therethrough. The connector is disposed at a proximal end of the catheter. The tapered locking sleeve has an interior surface, wherein the locking sleeve is coaxially disposed about the connector. An interior surface profile of the sleeve corresponds with an exterior surface profile of the connector such that the sleeve is capable of longitudinal sliding movement relative to the connector. The locking mechanism secures the locking sleeve to the connector in a locked position such that the tension member is secured between the interior surface of the locking sleeve and the exterior surface of the connector.

In a feature of this aspect, the connector and the locking sleeve include a generally conical shape. In another feature of this aspect, the locking mechanism includes at least a partial slot disposed in the exterior surface of the connector and a mating ridge extending from the interior surface of the locking sleeve, wherein when the locking sleeve slides such that the ridge of the sleeve is aligned with the mating slot of the connector, the ridge snaps into the slot for a secure fit.

In an additional feature of this aspect, the locking mechanism includes an interference fit between the interior surface of the sleeve and the exterior surface of the connector. In a further feature of this aspect, the locking assembly is dimensioned to fit within a 30 Fr access sheath. In other features, the connector may include an aperture through which a proximal portion of the tension member may pass and the sleeve may include a sealing element disposed on the interior surface thereof, wherein the sealing element is located such that it prevents any fluid contents of the catheter from inadvertently exiting the aperture when the sleeve is in the locked position.

In a fourth aspect of the invention, a drainage catheter includes an elongated tubular member and a locking assembly. The tubular member has a distal end for insertion into a patient, a proximal end, and a passageway extending longitudinally therethrough. The distal end is formed to be positioned into a desired configuration. The locking assembly is engaged with the proximal end of the tubular member and includes a tapered connector, a tapered locking sleeve, and a locking mechanism. The tapered connector has an exterior surface with a profile and a passageway extending longitudinally therethrough. The tapered locking sleeve has an interior surface with a profile, wherein the locking sleeve is coaxially disposed about the connector and the interior surface profile of the sleeve corresponds with the exterior surface profile of the connector such that the sleeve is capable of longitudinal sliding movement relative to the connector. The locking mechanism secures the locking sleeve to the connector in a locked position such that the tension member is secured between the interior surface of the locking sleeve and the exterior surface of the connector.

In a fifth aspect of the invention, a locking assembly for use with a tension member in a drainage catheter includes a connector and a clamping element. The connector has an exterior surface and a passageway extending longitudinally therethrough. The connector is disposed at a proximal end of the catheter. The clamping element is formed in the exterior surface of the connector whereby the tension member may be grasped by and secured by the clamping element.

DETAILED DESCRIPTION

Figure 1:
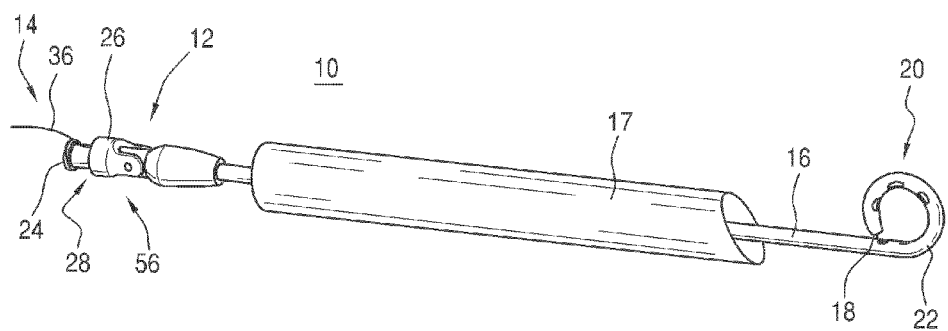
FIG. 1 is a perspective view of a drainage catheter in accordance with an embodiment of the present invention.

For the purposes of promoting an understanding of the principles of the invention, reference will now be made to the embodiments illustrated in the drawings, and specific language will be used to describe the same. It should nevertheless be understood that no limitation of the scope of the invention is thereby intended, such alterations and further modifications in the illustrated apparatus, and such further applications of the principles of the invention as illustrated therein being contemplated as would normally occur to one skilled in the art to which the invention relates.

In the following discussion, the terms "proximal" and "distal" will be used to describe the opposing axial ends of the drainage catheter, as well the opposing axial ends of component features of the catheter, such as the locking mechanism. The term "proximal" is used in its conventional sense to refer to the end of the catheter or component feature that is closest to the operator during use. The term "distal" is used in its conventional sense to refer to the end of the catheter or component feature that is initially inserted into the patient or that is closest to the patient during use.

In one aspect, the present invention relates to a catheter, such as a drainage catheter, having a locking assembly disposed at a proximal end of the catheter. The catheter has a tubular member, the distal end of which is lockable into a desired configuration, such as a loop or a pigtail, for retaining the catheter in a body cavity, such as the bladder. A flexible tension member, such as a suture, extends through the locking assembly and to the distal end of the tubular member for use in drawing the distal end into the desired configuration, whereupon the locking assembly is activated to maintain this configuration.

FIG. 1 is a perspective view of a drainage catheter 10 in accordance with an embodiment of the present invention. As illustrated, the drainage catheter 10 includes a locking assembly 12 positioned at a proximal end 14 of the catheter 10, and an elongated tubular member 16 extending in a distal direction from the locking assembly 12. Preferably, the tubular member 16 tapers to an open distal tip 18. As shown in FIG. 1, the locking assembly 12 is in the locked position 56, whereupon the distal end 22 of the tubular member 16 is locked into the desired configuration, in this case a loop. However, the distal end 22 assumes a straight configuration with a stiffening cannula during a well-known percutaneous technique for introduction of the drainage catheter 10 into a body cavity. Placing the distal end 22 of the tubular member 16 into the desired configuration, e.g., a loop or a pigtail, inhibits unintended withdrawal or displacement of the catheter 10 from its position in the desired body cavity, e.g. the bladder of a patient. The drainage catheter 10 is disposed within an access sheath 17, such as 30 Fr access sheath. The locking assembly 12 is dimensioned to fit within the 30 Fr access sheath.

Figure 2:
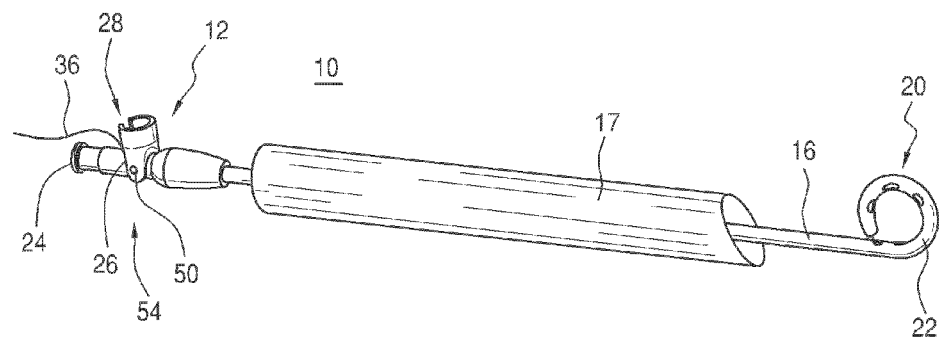
FIG. 2 is a perspective view of the drainage catheter of FIG. 1 with the locking assembly in an unlocked position.
Figure 3:
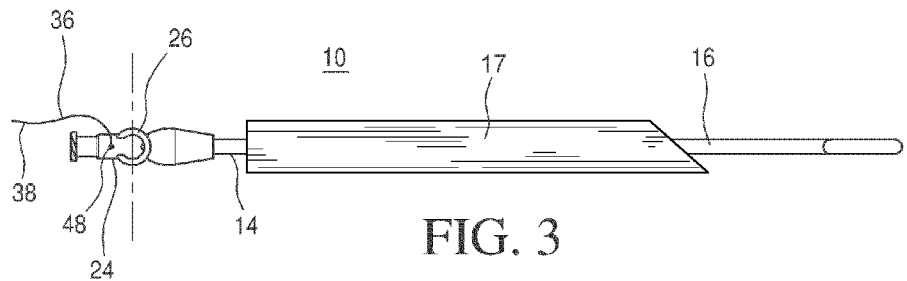
FIG. 3 is a top plan view of the drainage catheter of FIG. 2.
Figure 4:
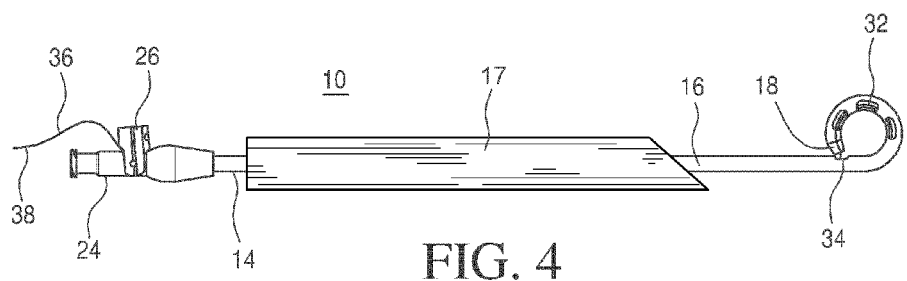
FIG. 4 is a side elevational view of the drainage catheter of FIG. 2.
Figure 5:
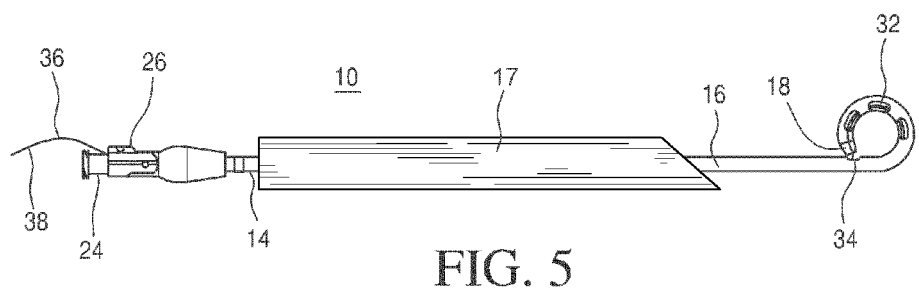
FIG. 5 is a side elevational view of the drainage catheter of FIG. 1.
Figure 6:
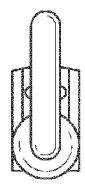
FIG. 6 is an end view of the drainage catheter of FIG. 4.
Figure 7:
FIG. 7 is an end view of the drainage catheter of FIG. 5.
Figure 3A:
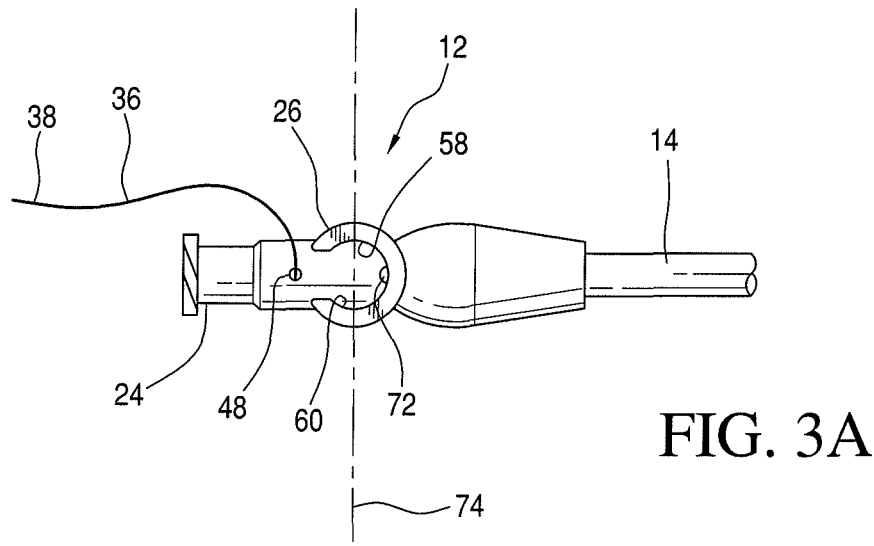
FIG. 3A is a more detailed view of the locking assembly of FIG. 3.
Figure 4A:
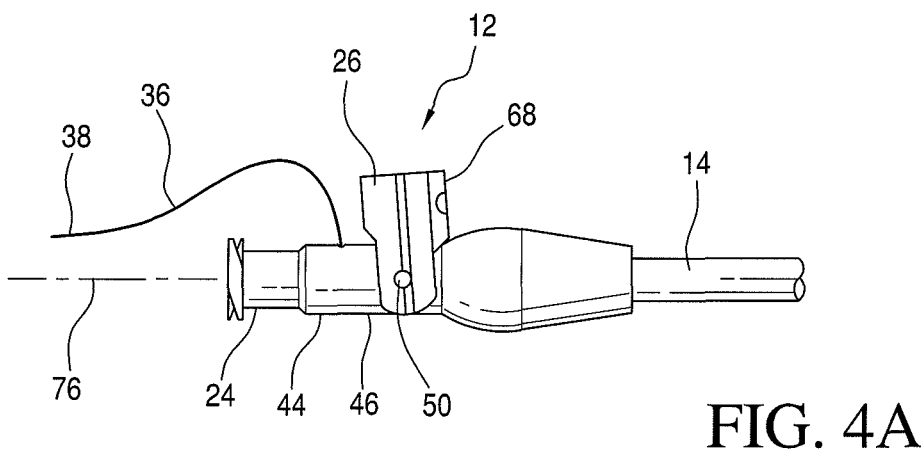
FIG. 4A is a more detailed view of the locking assembly of FIG. 4.
Figure 5A:
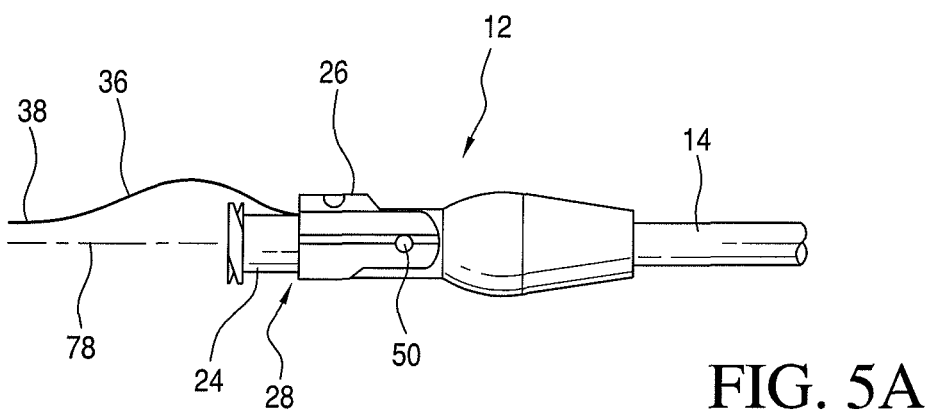
FIG. 5A is a more detailed view of the locking assembly of FIG. 5.

In the embodiment shown, the locking assembly 12 comprises a connector 24, a locking arm 26, and a locking mechanism 28. FIG. 2 is a perspective view of the drainage catheter of FIG. 1 with the locking assembly in an open position. FIG. 3 is a top plan view of the drainage catheter of FIG. 2. FIG. 4 is a side elevational view of the drainage catheter of FIG. 2. FIG. 5 is a side elevational view of the drainage catheter of FIG. 1. FIGS. 3A, 4A, and 5A provide detailed views of the locking assemblies of corresponding FIGS. 3, 4, and 5, respectively. FIG. 6 is an end view of the drainage catheter of FIG. 4. FIG. 7 is an end view of the drainage catheter of FIG. 5.

The tubular member 16 has a passageway extending longitudinally between the distal end 22 and the locking assembly 12. As shown in FIGS. 4 and 5, a plurality of drainage ports 32 communicating with the passageway are positioned proximate the distal end 22 for receiving fluid to be drained from the body cavity. The tubular member 16 further includes additional ports 34 positioned proximate the drainage ports 32 and the distal end 22 and communicating with the passageway. A tension member 36, such as a suture, extends along the passageway and through the ports 32, 34. The ports 32, 34 are spaced apart a predetermined length equal to the circumference of, e.g., the desired loop configuration. The tension member 36 includes a proximal portion 38 which extends outwardly from the locking assembly 12 for grasping and drawing the tension member 36 to form the desired loop configuration at the distal end 22 of the tubular member 16. The tension member 36 further includes a distal portion (not shown), which may be fixedly attached to the connector.

As shown in FIGS. 3A, 4A, and 5A, the connector 24 includes a longitudinal passageway extending therethrough. It further includes an exterior surface 44 having a profile 46. In the illustrated embodiment, the connector 24 has a generally cylindrical profile, such as with a luer connector. However, it will be appreciated that alternative exterior surface profiles are within the scope of the invention. The connector 24 further includes an aperture 48 disposed therein, through which the proximal portion 38 of the tension member 36 may pass. The proximal portion 38 of the tension member 36 passes through the passageway of the tubular member 16, through the passageway of the connector 24 and then through the aperture 48 of the connector 24, respectively, such that the proximal portion 38 may be grasped and pulled by a user thereby aiding in imparting the desired configuration to the distal end 22 of the tubular member 16. The locking assembly 12 further includes a mechanism for pivotably attaching the locking arm 26 to the connector 24. In an exemplary embodiment, the pivotable attachment mechanism comprises a pivot pin 50, which operably attaches the locking arm 26 to the connector 24 and provides an axis of rotation 74 about which the locking arm 26 may pivot or rotate to enable movement to and between an unlocked position 54 and a locked position 56.

The locking arm 26 has an interior surface 58 with a profile 60 that corresponds with or mates with the exterior surface profile 46 of the connector 24. In the illustrated embodiment, the interior surface profile 60 is curved to correspond with the cylindrical profile of the connector 24 and the locking arm 26 is partially cylindrical in shape; however, it will be appreciated that other interior surface profiles and locking arm shapes are within the scope of the invention.

The locking arm 26 is pivotably attached to the connector 24 such that the locking arm 26 pivots to and between the unlocked position 54 and the locked position 56. As shown in FIG. 5A, when the locking assembly 12 is in the locked position 56, the tension member 36 is secured between the interior surface 58 of the locking arm 26 and the exterior surface 44 of the connector 24. In addition, when the locking assembly 12 is in the locked position 56, the locking arm 26 fits flush against the connector 24. This arrangement is advantageous in maintaining the relatively small size of the locking assembly 12. In the illustrated embodiment, the locking arm 26 is disposed such that the axis of rotation 74 is orthogonal to the longitudinal axis 76 of the connector 24. Additionally, the locking arm 26 is disposed such that its longitudinal axis 78 is aligned with the longitudinal axis 76 of the connector 24 when the locking assembly 12 is in the locked position 56 (see FIG. 5A). While the pivotable attachment mechanism comprises a pivot 50 pin or pins in the, illustrated figures, it will be appreciated that other pivotable attachment mechanisms are within the scope of the invention. The locking arm 26 may further comprise a surface irregularity on its exterior surface 68 to aid in manipulating the locking arm 26, for example, to aid in disengaging the locking arm 26 from the locked position 56. For example, the locking arm 26 may include a raised lip or a series of ridges on its exterior surface. The raised lip or ridges may be at or near the proximal end of the locking arm 26; however, it will be appreciated that a raised lip or any other surface irregularity may be disposed in various locations along the exterior surface 68 of the locking arm 26. The locking arm 26 may further comprise a sealing element 72 disposed on the interior surface 58 thereof. It is preferred that the sealing element 72 be disposed at a location on the interior surface 58 such that it is in a sealing arrangement with the aperture 48 of the connector 24 when the locking arm 26 is in the locked position 56 thereby preventing fluid contents of the catheter 10 from inadvertently exiting through the aperture 48 when the locking arm 26 is in the locked position 56. It is contemplated that the sealing element 72 may comprise a resilient plug extending from the interior surface 58 of the locking arm 26. However, it will be appreciated that any component that is capable of forming a sealing arrangement with the aperture 48 of the connector 24 may serve as the sealing element 72.

In the illustrated embodiment, the locking mechanism 28 comprises an interference fit between the connector 24 and the locking arm 26 that secures the locking arm 26 against the connector 24 when it 26 is pressed against the connector 24 in the locked position 56. It is contemplated that the locking mechanism 28 may comprise a ridge and slot assembly. For example, the locking arm 26 may comprise a ridge extending from its interior surface 58 that is configured to fit into a corresponding slot formed in the exterior surface 44 of the connector 24 when the locking arm 26 is in the locked position 56. Alternatively, the connector 24 may comprise a ridge extending from its exterior surface 44 that is configured to fit into a corresponding slot formed into the interior surface 58 of the locking arm 26 when the locking arm 26 is in the locked position 56. It is contemplated that the locking mechanism 28 may comprise a combination of individual locking mechanisms, for example, the locking mechanism 28 may comprise an interference fit and a ridge and slot assembly. Further, it will be appreciated that any locking mechanism that aids in securing the locking arm 26 to the connector 24 in the locked position 56 without hindering operation of the drainage catheter 10 may be used.

Figure 8:
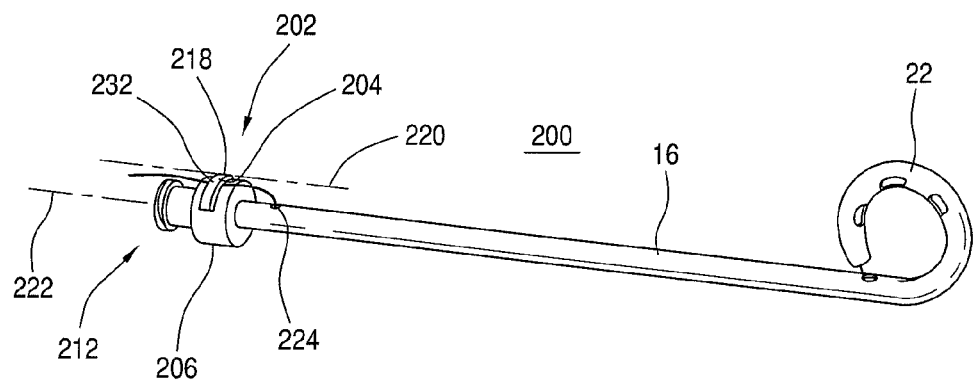
FIG. 8 is a perspective view of a drainage catheter in accordance with an alternative embodiment of the present invention.
Figure 9:
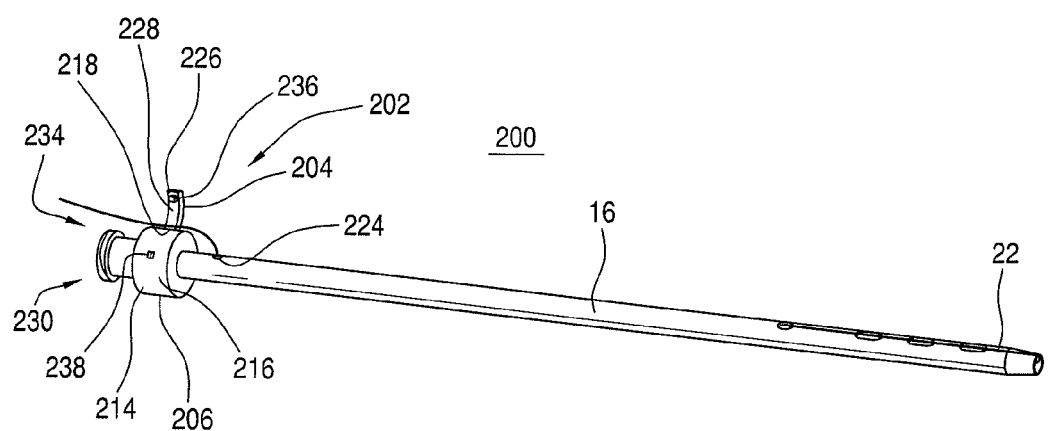
FIG. 9 is a perspective view of the drainage catheter of FIG. 8 with the locking assembly in an unlocked position.

FIGS. 8 and 9 are perspective views of a drainage catheter 200 in accordance with an alternative embodiment of the present invention. In this embodiment of the drainage catheter 200, the locking assembly 202 also comprises a locking arm 204 and a connector 206. The reference numerals that were used for the above embodiment will be used for like components in the instant embodiment. As illustrated, the drainage catheter 200 includes a locking assembly 202 positioned at a proximal end of the catheter 200, and an elongated tubular member 16 extending in a distal direction from the locking assembly 202. As shown in FIG. 8, the locking assembly 202 is in the locked position 212, whereupon the distal end 22 of the tubular member 16 is locked into the desired configuration, in this case a loop. As shown in FIG. 9, the locking assembly 202 is in an unlocked position 230 and the distal end 22 of the tubular member 16 is assuming a straight configuration, as it would be with a stiffening cannula disposed therein for insertion into a patient.

The connector 206 includes a longitudinal passageway extending therethrough. It further includes an exterior surface 214 having a profile 216. In the illustrated embodiment, the connector 206 has a cylindrical profile. However, it will be appreciated that other exterior surface profiles are within the scope of the invention. The connector 206 further includes a mechanism for pivotably attaching the locking arm 204 to the connector 206. In the illustrated embodiment, the pivotable attachment mechanism comprises a living hinge 218. The axis of rotation 220 of the living hinge 218 is parallel with a longitudinal axis 222 of the connector 206. A living hinge typically comprises a thin flexible plastic hinge that joins two rigid plastic parts together, thus allowing them to bend along the line of the hinge. Many plastic resins may be used to form living hinges. However, polyethylene and polypropylene resins are particularly well suited for forming living hinges. The living hinge 218 enables the connector 206 and the locking arm 204 to be integral with one another thus enabling a combined connector and locking arm component to be formed as a single component, for example, by injection molding.

In the illustrated embodiment, the tubular member 16 comprises a tension member port 224 through which the proximal portion 38 of the tension member 36 passes. The proximal portion 38 of the tension member 36 passes through the passageway of the tubular member 16 and then through the tension member port 224 of the tubular member 16 such that the proximal portion 38 may be grasped and pulled by a user thereby imparting the desired configuration to the distal end 22 of the tubular member 16. It is contemplated that a sliding sleeve (not shown) may be positioned over the port 224 to act as a sealing element to prevent fluids present in the tubular member 16 from exiting the port 224.

The locking arm 204 has an interior surface 226 with a profile 228 that corresponds with or mates with the exterior surface profile 216 of the connector 206. In the illustrated embodiment, the interior surface profile 228 is curved to correspond with the cylindrical profile of the connector 206 and the locking arm 204 is shaped as an elongated tab. The locking arm 204 is pivotably attached to the connector 206 via the living hinge 218 such that the locking arm 204 pivots to and between an unlocked position 230 and the locked position 212. When the locking arm 204 is in the locked position 212, the tension member 36 is secured between the interior surface 226 of the locking arm 204 and the exterior surface 214 of the connector. In the illustrated embodiment, when the locking arm 204 is in the locked position 212, it is flush against the connector 206. This arrangement is advantageous in maintaining a relatively small size for the locking assembly 202. As shown, the locking arm 204 is disposed such that the locking arm 204 is orthogonal to the longitudinal axis 222 of the connector 206. While the pivotable attachment mechanism comprises a living hinge 218 in the illustrated figures, it will be appreciated that other pivotable attachment mechanisms are within the scope of the invention.

It is contemplated that the locking arm 204 may further comprise a surface irregularity on its exterior surface 232 to aid in manipulating the locking arm 204, for example, to aid in disengaging the locking arm 204 from the locked position 212. For example, it is contemplated that the locking arm 204 may include a raised or extending lip or a series of ridges on its exterior surface. The raised or extending lip or ridges may be at or near the proximal end of the locking arm; however, it will be appreciated that a raised or extending lip or any other surface irregularity may be disposed in various locations along the exterior surface of the locking arm 204.

In the illustrated embodiment, the locking mechanism 234 comprises a ridge and slot assembly. In particular, the slot is a notch 238 formed in the exterior surface 214 of the connector 206 and the ridge 236 extending from the interior surface 226 of the locking arm 204 is appropriately sized to fit into the notch of 238 the connector 206 in a snap fit arrangement.

A method of using the drainage catheter 10 with the locking assembly 12 will now be described. Initially, the distal end 22 of the tubular member 16 is percutaneously inserted into a body cavity, such as the bladder. This step is typically performed by inserting the distal end of a thin-walled hollow needle through the abdominal wall and into the bladder in a well-known manner. A wire guide is then inserted through the needle into the bladder, and the needle is removed, leaving the wire guide in place. A dilator and an access sheath may be used alone or in combination over the wire guide to increase the size of the puncture site. Existing locking assemblies or mechanisms are often large and bulky and hence not able to be used with access sheaths that are 30 Fr or smaller without modifying or deforming the access sheath in some way. Advantageously, the locking assemblies described herein are small enough that they may be used with 30 Fr access sheaths without modification.

During percutaneous insertion of the tubular member distal end 22 over the wire guide, the catheter 10, 200 will typically be manipulated into a generally straight configuration, with the locking assembly 12, 202 in the unlocked position as shown. This generally straight configuration may be achieved by inserting a flexible stiffener (not shown) through the aligned passageways and of the connector 24, 206 and the elongated tubular member 16, respectively. Following insertion of the straightened distal end 22 of the tubular member 16 into the bladder, the wire guide and flexible stiffener are removed from the patient. The distal end 22 of the tubular member 16 is left in place for providing fluid flow from the bladder through the ports 32, 34 and the distal tip 18 to a conventional fluid collection system (not shown), such as a proximally extending piece of tubing and a plastic collection bag.

In order to inhibit unintended withdrawal or dislodgement of the distal end 22 of the tubular member 16 from the bladder, the locking assembly 12, 202 is activated to achieve the desired distal end configuration, such as the loop shown in FIG. 1.

To achieve this configuration, the operator grasps and pulls on the proximal portion 38 of the tension member 36, while the locking assembly 12, 202 is still in the unlocked, or open, position 54, 230. As the tension member proximal portion 38 is pulled, the tension member 36 is moved or drawn proximally to form the distal end 22 of the tubular member 16 into the desired loop configuration. In order to maintain the distal end 22 of the tubular member 16 in the desired loop configuration, the locking arm 26, 204 is moved or pushed into the locked position 56, 212 whereby the interior surface 58, 226 of the locking arm 26, 212 is pressed against the exterior surface 44, 214 of the connector 24, 206 and the tension member 36 is secured or "locked" between the locking arm 26, 204 and the connector 24, 206. As a result, further pulling or other movement of the tension member 36 is substantially prevented, thereby maintaining the tension that forms the loop.

Figure 10:
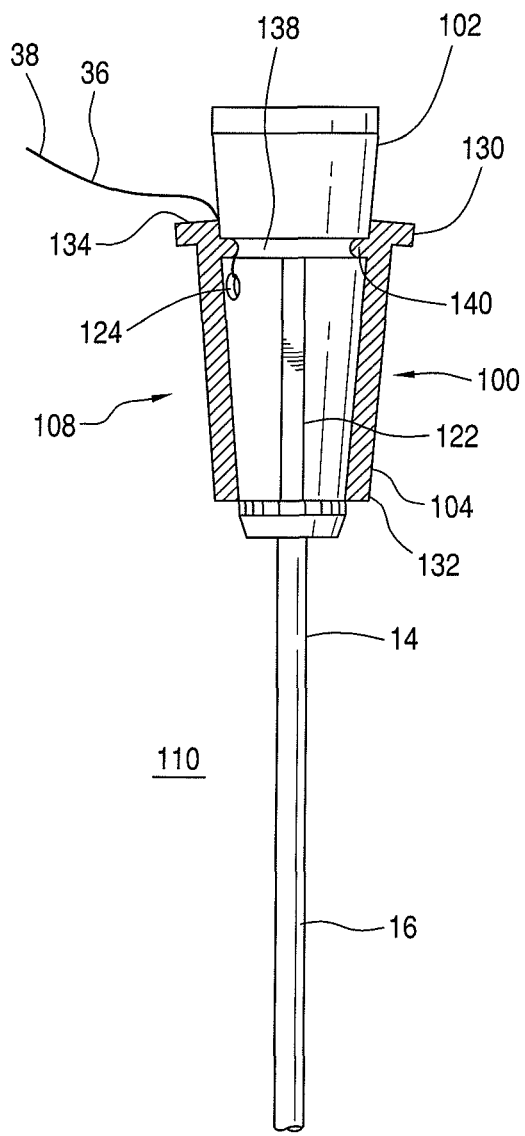
FIG. 10 is a side elevational view of a locking assembly in accordance with an alternative embodiment of the present invention, with the locking sleeve shown in cross-section.
Figure 11:
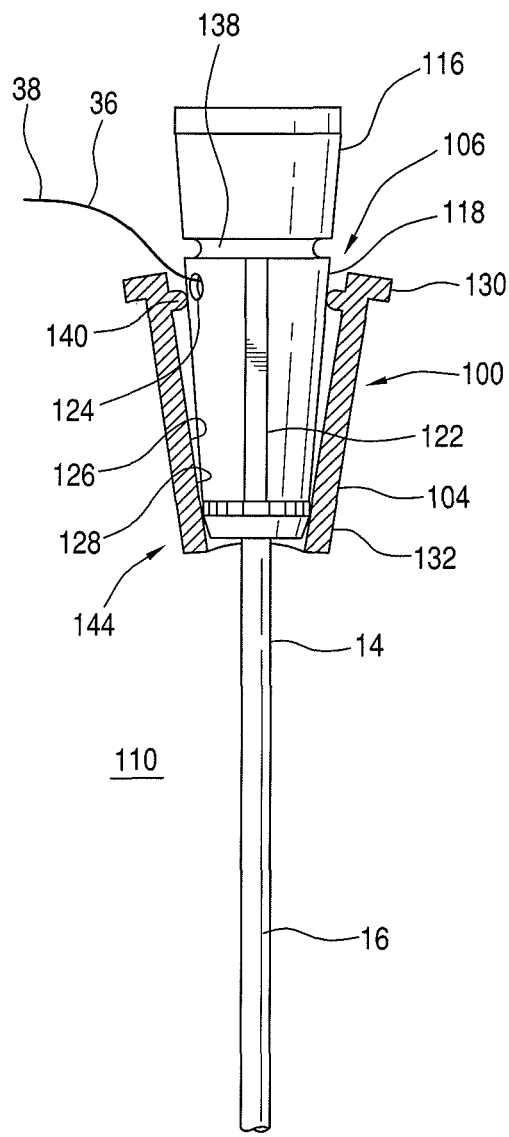
FIG. 11 is a side elevational view of the locking assembly of FIG. 10 in an unlocked position, with the locking sleeve shown in cross-section.

FIGS. 10 and 11 are side views of a locking assembly in accordance with an alternative embodiment of the present invention with a locking sleeve being shown in cross-section. FIG. 10 shows a locking assembly 100 in a locked position 108 and FIG. 11 shows the locking assembly 100 in an unlocked position 144. The locking assembly 100 comprises a tapered connector 102, a tapered locking sleeve 104, and a locking mechanism 106 for securing the sleeve 104 to the connector 102 in a locked position 108 such that a tension member 36 is secured between the sleeve 104 and the connector 102. As with the previously described embodiment, this embodiment includes a catheter 110 having a locking assembly 100 disposed at a proximal end 14 of an elongated tubular member 16. The reference numerals that were used above will be used for like components in the instant embodiment.

The connector 102 comprises an exterior surface 116 having a tapered profile 118 and a passageway extending longitudinally therethrough. In the illustrated embodiment, the connector 102 is conical in shape. However, it will be appreciated that the connector 102 may have any tapered surface profile that will not hinder use of the locking assembly 100. For example, the connector 102 may have a profile 118 comprising a tapered oval or ellipse. It is contemplated that the connector 102 may comprise a track 122 along its exterior surface 116 that is capable of guiding sliding movement of the sleeve 104 along the connector 102. The connector 102 may further include an aperture 124 disposed therein, through which the proximal portion 38 of the tension member 36 may pass. The proximal portion 38 of the tension member 36 passes through the passageway of the tubular member 16, through the passageway of the connector 102 and then through the aperture 124 of the connector 102, respectively, such that the proximal portion 38 may be grasped and pulled by a user thereby imparting the desired configuration to the distal end of the tubular member 16.

The locking sleeve 104 comprises an interior surface 126 having a tapered profile 128. The sleeve 104 is coaxially disposed about the connector 102 such that the exterior surface 116 of the connector 102 and the interior surface 126 of the locking sleeve 104 are in opposing facing relation with one another. The sleeve 104 is configured for longitudinal sliding movement relative to the connector 102. In the illustrated embodiment, the locking sleeve 104 is generally conical in shape. However, it will be appreciated that the sleeve 104 may have any tapered surface profile 128 that will not hinder use of the locking assembly 100. The sleeve 104 may comprise a lip 130 extending from an exterior surface 132 to aid in manipulating the sleeve 104, for example, for aiding in moving the sleeve 104 to the locked position 108 or out of the locked position 108. It is contemplated that the lip 130 may be disposed at a rim 134 of the sleeve 104. The sleeve 104 may further comprise a sealing element (not shown) disposed on the interior surface 126 thereof. It is preferred that the sealing element be disposed at a location on the interior surface 126 such that it is in a sealing arrangement with the aperture 124 of the connector 102 when the sleeve 104 is in the locked position 108 thereby preventing fluid contents of the catheter 110 from inadvertently exiting through the aperture 124 when the sleeve 104 is in the locked position 108. It is contemplated that the sealing element may comprise a resilient plug extending from the interior surface 126 of the sleeve 104. However, it will be appreciated that any component that is capable of forming a sealing arrangement with the aperture 124 of the connector 102 may serve as the sealing element.

In FIGS. 10 and 11, the locking mechanism 106 comprises a slot and ridge assembly. In particular, the connector 102 includes a slot 138 about the exterior surface 116, and the sleeve 104 includes a ridge 140 extending about the interior surface 126 thereof. Alternatively, the slot 138 may be disposed about the interior surface 126 of the sleeve 104 and the ridge 140 may be disposed about the exterior surface 132 of the connector 102. The slot 138 and the ridge 140 may extend completely around the particular component or may partially extend around the component. In the embodiment wherein the ridge 140 and the slot 138 only extend partially about the particular components, the track 122 of the connector 102 may provide a means of maintaining alignment between the partial ridge 140 and slot 138. The locking mechanism 100 may, alternatively, comprise an interference fit between the connector 102 and the sleeve 104. As with the above-described locking assembly 12, it is contemplated that the locking mechanism 106 may comprise a combination of locking mechanisms, for example, the locking mechanism may comprise an interference fit and a ridge and slot assembly. Further, it will be appreciated that any locking mechanism that aids in securing the sleeve 104 to the connector 102 in the locked position 108 thereby securing the tension member 36 without hindering operation of the drainage catheter 110 may be used.

A method of using the drainage catheter 110 with the locking assembly 100 will now be described. Insertion of the catheter 110 into the body is the same for this catheter 110 as that described above for catheter 10. Thus, for the sake of brevity, it will not be repeated.

Once the distal end 22 of the tubular member 16 is inserted into the desired location, the locking assembly 100 is activated to achieve the desired distal end configuration to inhibit unintended withdrawal or dislodgement of the distal end 22 of the tubular member 16 from the location.

To achieve this configuration, the operator grasps and pulls on the proximal portion 38 of the tension member 36, while the locking assembly 100 is still in an unlocked, or open, position. As the tension member proximal portion 38 is pulled, the tension member 36 is moved or drawn proximally to form the distal end 22 of the tubular member 16 into the desired loop configuration. In order to maintain the distal end 22 of the catheter 110 in the desired loop configuration, the sleeve 104 is moved or pushed longitudinally toward a proximal end 142 of the connector 102 until it reaches the locked position 108 whereby the interior surface 126 of the sleeve 104 is pressed against the exterior surface 116 of the connector 102, the ridge 140 of the sleeve 104 is snapped into the slot 138 of the connector 102, and the tension member 36 is secured or "locked" between the sleeve 104 and the connector 102, including the ridge 140 and slot 138 components thereof. As a result, further pulling or other movement of the tension member 36 is substantially prevented, thereby maintaining the tension that forms the loop.

Figure 12:
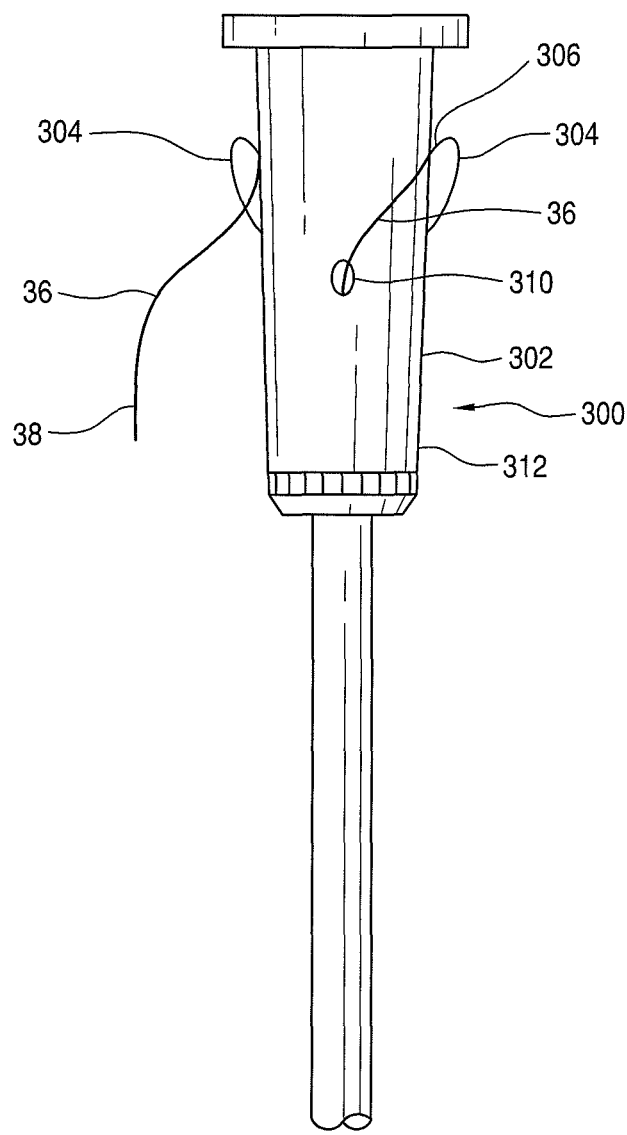
FIG. 12 is a side elevational view of a locking assembly in accordance with an alternative embodiment of the present invention.

FIG. 12 is a side elevational view of a locking assembly 300 in accordance with another alternative embodiment of the present invention. The locking assembly 300 comprises a connector 302 having a longitudinal passageway extending therethrough and a clamping element 304 formed in an exterior surface 312 of the connector 302 for securing the tension member 36. It is contemplated that the clamping element 304 may comprise a wing-like element(s) protruding from the connector 302 or a slit(s) formed therein. If the clamping element is a slit or plurality of slits, it is preferred that the slits not pass completely through the connector. It will be appreciated that the clamping element 304 may take many forms. The connector 302 may comprise a luer connector with the clamping element 304 formed therein. The connector 302 may further include an aperture 310 disposed therein, through which the proximal portion 38 of the tension member 36 may pass. The proximal portion 38 of the tension member 36 may pass through the passageway of the tubular member 16, through the passageway of the connector 302 and then through the aperture 310 of the connector 302, respectively, such that the proximal portion 38 may be grasped and pulled by a user thereby imparting the desired configuration to the distal end of the tubular member 16. The proximal portion 38 of the tension member 36 may then be wrapped about the connector 302 and secured by sliding the proximal portion 38 into a clamping portion 306 of the clamping element 304 to maintain the desired distal end configuration.

Those skilled in the art will recognize that not every feature of the catheter will be required in every instance, nor will every operating step described be required in every instance of use. Routine modifications may be made to the structure and the method of use from time to time, with all of the foregoing being considered to be within the scope of the invention. Those skilled in the art will appreciate that the various components of the catheter and locking mechanism described herein may be fabricated from many possible materials that are suitable for such use, using standard techniques. Typically, various medical grade polymeric materials are desirable. For example, the connector, locking arm, and/or the sleeve may be formed from polyurethane, polypropylene, polyethylene, nylon, polyethylene terephthalate, polyethene, latex, and any other suitable polymer and/or combinations thereof. Alternatively, the components may be constructed of metal or a combination of metal and polymeric materials. Flexible tubular members suitable for use herein are well known in the art. The tubular member may be formed from any well-known material or combination of well-known materials, such as, for example, polyurethane.

It is to be understood that the above-described drainage catheter is merely an illustrative embodiment of the principles of this invention and that other connectors, catheters, and drainage apparatus may be devised by those skilled in the art without departing from the spirit and scope of this invention. In particular, the distal end of the catheter may be preformed into any desired configuration for positioning and retaining the distal end of the catheter in any part of a patient's body. It is further contemplated that the flexible tension member may be attached in any one of a number of well-known ways to the distal end of the tubular member and drawable through one or more ports in the tubular member for positioning the distal end in the desired position. It is also further contemplated that the medical device of the present invention has application as an abscess or biliary drainage catheter, a nephrostomy tube in the renal pelvis, a gastrostomy feeding tube, or any other catheter requiring a distally positioned retention means such as a pigtail or loop.

We claim:

1. A locking assembly for use with a tension member in a drainage catheter, comprising:
   (a) a connector disposed at a proximal end of the catheter, the connector having an exterior surface profile and a passageway extending longitudinally therethrough;
   (b) a locking arm having an interior surface profile that corresponds with the exterior surface profile of the connector, the locking arm being pivotably attached to the connector to enable pivoting movement of the locking arm about an axis of rotation, to and between an unlocked position and a locked position whereby when the locking arm is in the locked position, the tension member is secured between the interior surface of the locking arm and the exterior surface of the connector; and
   (c) a locking mechanism for preventing the locking arm from inadvertently disengaging from the locked position,
   wherein a longitudinal axis of the locking arm is generally aligned with a longitudinal axis of the connector when the locking assembly is in the locked position.

2. The locking assembly of claim 1, wherein the exterior surface profile of the connector is cylindrical and the interior surface profile of the locking arm is curved to correspond with the cylindrical exterior surface profile of the connector.

3. The locking assembly of claim 1, wherein the locking assembly is dimensioned to fit within a 30 Fr access sheath.

4. The locking assembly of claim 1, wherein the connector includes an aperture through which a proximal portion of the tension member may pass.

5. The locking assembly of claim 4, wherein the locking arm is in covering relation with the aperture when the locking arm is in the locked position.

6. The locking assembly of claim 5, wherein the locking arm includes a sealing element disposed on the interior surface thereof, and wherein the sealing element prevents fluid contents of the catheter from inadvertently exiting the aperture when the locking arm is in the locked position.

7. The locking assembly of claim 1, wherein the locking arm is positioned such that the axis of rotation thereof is generally orthogonal to a longitudinal axis of the connector.

8. The locking assembly of claim 1, wherein the shape of the locking arm is at least partially cylindrical.

9. The locking assembly of claim 1, wherein the locking arm is positioned such that the axis of rotation thereof is generally parallel with a longitudinal axis of the connector.

10. The locking assembly of claim 1, wherein the locking mechanism comprises an interference fit between the connector and the locking arm.

11. The locking assembly of claim 1, wherein when the locking arm is in the locked position, the locking arm is flush against the connector.

* * * * *